US006635489B2

(12) United States Patent
Whitney

(10) Patent No.: US 6,635,489 B2
(45) Date of Patent: Oct. 21, 2003

(54) MATERIALS FOR ENHANCING STAINING OF BIOPOLYMERS IN MATRICES

(75) Inventor: Scott Whitney, San Diego, CA (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 09/988,746

(22) Filed: Nov. 20, 2001

(65) Prior Publication Data

US 2002/0137222 A1 Sep. 26, 2002

Related U.S. Application Data

(60) Provisional application No. 60/249,452, filed on Nov. 20, 2000.

(51) Int. Cl.[7] .............................................. G01N 33/68
(52) U.S. Cl. .............................. 436/86; 436/8; 436/80; 436/94; 436/164; 436/166; 436/174; 422/61; 435/6; 435/810; 252/408.1
(58) Field of Search ............................. 436/8, 80, 86, 436/94, 164, 166, 169, 173, 174, 176, 177, 178, 905; 422/61; 435/6, 810; 252/408.1

(56) References Cited

U.S. PATENT DOCUMENTS

| | | | | |
|---|---|---|---|---|
| 3,835,143 A | * | 9/1974 | Witzel et al. | 546/297 |
| 4,007,135 A | * | 2/1977 | Hayden et al. | 502/317 |
| 4,405,720 A | | 9/1983 | Merril | 436/86 |
| 4,416,998 A | * | 11/1983 | Adams et al. | 422/61 |
| 4,434,234 A | * | 2/1984 | Adams et al. | 422/61 |
| 4,468,466 A | | 8/1984 | Morrissey | 436/86 |
| 4,575,452 A | | 3/1986 | Lee et al. | 422/61 |
| 4,582,808 A | * | 4/1986 | Oosawa et al. | 436/169 |
| 4,703,016 A | | 10/1987 | Merril | 436/86 |
| 4,853,413 A | * | 8/1989 | Katz et al. | 514/526 |
| 5,064,768 A | * | 11/1991 | Ebata et al. | 422/61 |
| 5,200,296 A | * | 4/1993 | Nagamatsu et al. | 430/232 |
| 5,486,460 A | * | 1/1996 | Townsend | 435/40.51 |
| 5,492,810 A | * | 2/1996 | Caetano-Anolles et al. | 204/456 |
| 5,545,308 A | * | 8/1996 | Murphy et al. | 205/125 |
| 5,567,585 A | * | 10/1996 | Caetano-Anolles et al. | 204/462 |
| 6,127,122 A | * | 10/2000 | Park et al. | 435/6 |
| 6,316,267 B1 | * | 11/2001 | Bhalgat et al. | 422/61 |

OTHER PUBLICATIONS

Bergman, A.-C. et al., "Identification of gel-separated tumor marker proteins by mass spectrometry," *Electrophoresis* 21:679–686, Wiley-VCH (Feb. 2000).
Carr, S.A. and Annan, R.S., "Overview of Peptide and Protein Analysis by Mass Spectrometry," in *Current Protocols in Protein Science*, Coligan, J.E. et al., Eds., John Wiley & Sons, Inc., New York, NY, pp. 16.1.1–16.1.27 (1996).
*Expressions*, "Mass Spectrometry-Compatible Silver Staining," Invitrogen Newletter for Gene Cloning, Expression, and Analysis, vol. 7, p. 9, Nov. 2000.
Fernandez, J. and Mische, S.M., "Enzymatic Digestion of Proteins on PVDF Membranes," in *Current Protocols in Protein Science*, Coligan, J.E. et al., Eds., New York, NY, pp. 11.2.1–11.2.10 (1995).
Gharahdaghi, F. et al., "Mass spectrometric identification of proteins from silver-stained polyacrylamide gel: a method for the removal of silver ions to enhance sensitivity," *Electrophoresis* 20:601–605, Wiley-VCH (Mar. 1999).
Hellman, U. et al., "Improvement of an "In-Gel" Digestion Procedure for the Micropreparation of Internal Protein Fragments for Amino Acid Sequencing," *Anal. Biochem.* 224:451–455, Academic Press, Inc. (1995).
Merril, C.R. et al., "Silver Staining Methods for Polyacrylamide Gel Electrophoresis," *Meth. Enzymol.* 96:230–239, Academic Press, Inc. (1983).
Oakley, B.R. et al., "A Simplified Ultrasensitive Silver Stain for Detecting Proteins in Polyacrylamide Gels," *Anal. Biochem.* 105:361–363, Academic Press, Inc. (1980).
Patterson, S.D. and Aebersold, R., "Mass spectrometric approaches for the identification of gel-separated proteins," *Electrophoresis* 16:1791–1814, VCH (1995).
Rabilloud, T., "Mechanisms of protein silver staining in polyacrylamide gels: A 10–year synthesis," *Electrophoresis* 11:785–794, VCH (1990).
Rabilloud, T. et al., "Silver-Staining of Proteins in Polyacrylamide Gels: A General Overview," *Cell. Mol. Biol.* 40:57–75, Cellular and Molecular Biology (1994).
Riviere, L.R., "Enzymatic Digestion of Proteins in Solution," in *Current Protocols in Protein Science*, Coligan, J.E. et al., Eds., New York, NY, pp. 11.1.1–11.1.19 (1995).
Scheler, C. et al., "Peptide mass fingerprint sequence coverage from differently stained proteins on two-dimensional electrophoresis patterns by matrix assisted laser desorption/ionization-mass spectrometry (MALDI-MS)," *Electrophoresis* 19:918–927, Wiley-VCH (1998).
Shevchenko, A. et al., "Mass Spectrometric Sequencing of Proteins from Silver-Stained Polyacrylamide Gels," *Anal. Chem.* 68:850–858, American Chemical Society (1996).
Sigma Catalog, Products for Life Science Research, pp. 962–965 (2000–2001).
Stone, K.L. and Williams, K.R., "Digestion of Proteins in Gels for Sequence Analysis," in *Current Protocols in Protein Science*, Coligan, J.E. et al., Eds., New York, NY, pp. 11.3.1–11.3.13 (1995).
Wood, H.W., "The Examination of Gelatin Extracts and Polythionates by means of Paper Electrophoresis," *J. Photo. Science* 2:154–159, The Royal Photographic Society of Great Britain (1954).

* cited by examiner

*Primary Examiner*—Maureen M. Wallenhorst
(74) *Attorney, Agent, or Firm*—Sterne, Kessler, Goldstein & Fox P.L.L.C.

(57) ABSTRACT

Methods for detecting biopolymers in a matrix are disclosed, which involve contacting the matrix with a sensitizing reagent, which may include one or more optionally substituted heteroaromatic compounds; contacting the matrix with one or more reduceable metal salts to stain the biopolymer; and detecting the stained biopolymer. Also disclosed are compositions for carrying out the invention and compositions made according to the invention. Also disclosed are kits for carrying out the methods of the invention.

51 Claims, No Drawings

MATERIALS FOR ENHANCING STAINING OF BIOPOLYMERS IN MATRICES

BACKGROUND OF THE INVENTION

1. Field of the Invention

The invention is in the field of metallic stains for biopolymers such as proteins, polypeptides and nucleic acid molecules when fixed in synthetic matrixes.

2. Related Art

Gel electrophoresis is a commonly used analytical technique in biochemistry and related fields of study for the separation of nucleic acids, polypeptides, proteins and oligosaccharides. A sample of interest is placed in a matrix and exposed to an electric field which causes various components to migrate and separate into distinct bands dependent upon the molecular weight, charge, and other physical properties of the molecules. After electrophoresis has ended, the pattern of migration is not typically decipherable because the majority of molecules have no integral chorormophores or fluorophores by which they may be visualized. Numerous methods have been developed to visualize the exact locations of the molecules of interest within a matrix while leaving the blank areas of the matrix virtually unstained. These include the Coomassie Brillant Blue dyes, ethidium bromide and Ponceau S stains. Silver staining was developed to increase the sensitivity over that achieved with these dyes. One of the earliest and widely used silver staining technique was reported by Merril et al., *Meth. Enzymol.* 96:230 (1983). In this report, an electrophoretic matrix, specifically polyacrylamide, is immersed in either an acid or an acid/alcohol solution for about one hour to fix the proteins within the matrix. The matrix is then washed typically for about thirty minutes. The matrix is then soaked for about five minutes in a dichromic acid solution to oxidize the protein. Next, the gels are soaked in a silver nitrate solution for twenty minutes and then rinsed with a sodium carbonate/formaldehyde buffer to reduce silver ions bound to proteins and nucleic acids. A silver pattern is allowed to develop and then stopped by the addition of acetic acid. The pattern is then analyzed either by direct visualization or by instrumental techniques.

The method of Merril et al. was simplified by Oakley et al., *Anal. Biochem.* 105: 361(1980). Electrophoresed gels were treated with unbuffered glutaraldehyde to cross-link proteins. Following rinsing, the gels were treated with a silver nitrate/ammonium hydroxide/sodium hydroxide solution. Finally, a solution of formaldehyde in citric acid is used to reduce silver ion to silver and visualize the bands within the gel matrix.

Glutaraldehyde has been employed by many laboratories to lower the limit of detection of proteins by silver staining (Rabilloud, T., *Electrophoresis* 11:785–794 (1990); Rabilloud, T., *Cell. Mol. Biol.* 40:57–75(1994)). The exact mechanism by which this compound enhances sensitivity has not been evaluated extensively, but it is thought to function by first binding to free amino groups in the protein to form a Schiff base leaving a free aldehyde function. Free amino groups are found at the N-terminus of the protein and also on the side chain of lysines and arginines. This aldehyde may reduce silver in the protein zone leading to an initiation of silver metal deposition. Silver metal is thought to catalyze further reduction of silver ion to silver so the net result is to increase the rate of silver deposition adjacent to the protein. An example of such a product employing glutaraldehyde sensitization is the SILVERXPRESS silver stain sold by Invitrogen Corporation, Carlsbad, Calif.

Use of glutaraldehyde, though it improves sensitivity of the stain to low levels of proteins, has an undesirable effect when further analysis of the gel by mass spectrometry is desired. Scheler et al., *Electrophoresis* 19:918–927 (1998). A widely used technique for the analysis of proteins by mass spectrometry is to cleave the protein into fragments with the enzyme trypsin. The fragments of a protein created by tryptic cleavage are readily predicted because the enzyme preferentially cleaves the amide bond immediately after a basic amino acid such as lysine or arginine. If the amino group of lysine or arginine is bound in a Schiff base by glutaraldehyde, it is no longer a cleavage site for trypsin. In addition, when an initial complex is formed between the glutaraldehyde molecule and the protein, the remaining free aldehyde group is available to condense with other amino groups thereby producing crosslinked proteins. This property is what makes glutaraldehyde such an effective fixative for histological applications. However by crosslinking peptides and proteins containing amino groups in a random fashion, not only are the potential trypsin cleavage sites blocked, crosslinked peptides and peptides are randomly created whose molecular weight may not be predicted from an analysis of the protein primary structure. As a result, there is a reduced abundance of many fragments whose molecular weight would be diagnostic for the identity of the protein. Although other enzymes can be used to fragment the protein, the specificity of trypsin makes it a favored choice.

U.S. Pat. No. 4,405,720 discloses a silver staining method for polypeptides in gels comprising photo-reversing the polypeptide-gel by treatment with an oxidizing reagent, forming a latent stain image by treating the polypeptide-gel with a reduceable metal salt termed a photosensitive salt, and developing the stain image by treating the polypeptide gel with a reducing agent. Examples of such photosensitive salts include salts of silver, gold, platinum, palladium and/or iridium.

U.S. Pat. No. 4,468,466 discloses a silver staining method comprising treatment with the reducing agent dithiothreitol followed by treatment with a silver salt and actuating radiation. According to this patent, dithiothreitol acts as a reducing agent to effect photoreversal and avoid silver staining of non-proteins.

U.S. Pat. No. 4,703,016 discloses a silver staining procedure for proteins and DNA. The process comprises fixing a protein on a membrane in cupric acetate solution; contacting the membrane with a solution comprising acetic acid, sodium chloride, and citric acid; contacting the membrane with a solution comprising acetic acid and silver nitrate and irradiating with a light source; contacting the membrane with a solution comprising acetic acid, sodium chloride and citric acid; transferring the membrane back to the silver nitrate solution and irradiating the membrane; developing the image by transferring to a solution comprising hydroquinone and formaldehyde; washing with water, contacting with sodium thiosulfate; and then washing with water.

U.S. Pat. No. 4,575,452 discloses methods of detection of proteins and nucleic acids in a matrix comprising fixing the proteins and nucleic acids in the matrix with aromatic sulfonic acid compounds having tertiary amines and N,N'-di-(9-acridyl)-diaminoalkylene compounds. Particular examples of such compounds include 4,4'-[1,4-phenylenebis(2,5-oxazolediyl)]-bisbenzene-sulfonic acid, 4,4'-[1,4-phenylenebis(4-methyl-2,5-oxazolediyl)]bisbenzene-sulfonic acid, 2,2'-(2,5-thiophenediyl)bis[5-(1,1-dimethylethyl)-7-benzoxazole-sulfonic acid, N,N,N-trimethyl-2-phenyl-5-(4-sulfophenyl)-4-oxazolemethanamonium hydroxide, 2,2'-(1,4-phenylene)bis

[N,N,N-trimethyl-5-(4-sulfophenyl)]-4-oxazolemethanamonium hydroxide, and N,N'-di-(9-acridyl)-1,6-diaminohexane.

SUMMARY OF THE INVENTION

The invention relates in part to the discovery that it is possible to provide a sensitivity of detection comparable or better than provided by glutaraldehyde fixation prior to staining without causing crosslinking of peptides or blockage of trypsin cleavage sites.

It has also been discovered that compounds possessing an aromatic structure containing heteroatoms capable of binding to silver ion can be used to improve the sensitivity of silver staining without impeding the cleavage of the protein by trypsin.

The present invention relates to a method for detecting a biopolymer in a matrix, comprising:
 (a) contacting the matrix with a sensitizing reagent comprising one or more optionally substituted heteroaromatic compounds;
 (b) contacting the matrix with one or more reduceable metal salts to stain said biopolymer; and
 (c) detecting the stained biopolymer.

The present invention further relates to the analysis by mass spectrometry of the biopolymer detected according to the present invention. In this embodiment, the biopolymer is recovered from the matrix, cleaved with a cleaving reagent, and subjected to mass spectrometric analysis. In a preferred embodiment, the biopolymer is a protein or peptide and the cleaving reagent comprises trypsin. Thus, in a further preferred embodiment, the invention relates to a method for identifying a protein or peptide in a matrix, comprising:
 (a) contacting the matrix with a sensitizing reagent comprising one or more optionally substituted heteroaromatic compounds;
 (b) contacting the matrix with one or more reduceable metal salts to stain said protein or peptide;
 (c) detecting the stained protein or peptide;
 (d) carrying out a cleavage reaction on the protein or peptide to give fragments; and
 (e) carrying out a mass spectrometric analysis on said fragments thereby identifying the protein or peptide.

The present invention also includes a kit for the detection of biopolymers comprising one or more components selected from the group consisting of
 (a) a sensitizing reagent comprising one or more optionally substituted heteroaromatic compounds;
 (b) one or more reduceable metal salts;
 (c) one or more developer solutions comprising a reducing agent;
 (d) one or more stopper solutions which prevent further reduction
 (e) of the reduceable metal salts;
 (f) one or more contrast enhancing agents;
 (g) one or more buffers;
 (h) one or more fixing reagents;
 (i) one or more cleaving reagents;
 (j) one or more biopolymers;
 (k) one or more matrixes; and
 (l) one or more indicators which are sensitive to pH changes.

The invention also relates to compositions for carrying out the methods of the invention as well as the compositions made according to the invention. Such compositions of the invention may comprise one or more of the components of the kit listed above.

DETAILED DESCRIPTION OF THE INVENTION

Techniques for electrophoretically separating proteins, polypeptides and nucleic acids in a matrix are well known. In gel electrophoresis, the molecules are separated into bands according to the rate at which an imposed electric field causes them to migrate through a matrix. A particularly preferred matrix useful in the present invention is polyacrylamide gel. Other useful matrices include agarose, paper, cellulose acetate, nitrocellulose, etc.

Examples of biopolymers that may be detected according to the present invention include nucleic acid molecules (e.g. DNA, RNA, hybrid DNA-RNA, DNA and RNA derivatives such as phosphothioates and mixed backbone derivatives), proteins, peptides and the like.

To fix biopolymers to a matrix, the matrix may be contacted with a fixing reagent or treated with microwave radiation. Such fixing reagents function to immobilize the biopolymer to the matrix and also remove substances which may interfere with the staining procedure. Such fixing reagents include any conventional fixing reagents such as, for example, glutaraldehyde, oxides of heavy metals such as mercury, lead and osmium, formaldehyde, paraformaldehyde, trichloroacetic acid and acetic acid. In another embodiment, the fixing reagent may be an aromatic sulfonic acid compound or a N,N'-di-(9-acridyl)-diaminoalkylene compound disclosed in U.S. Pat. No. 4,575,452. In a preferred embodiment, the fixing reagent comprises an aqueous solution of an organic acid and a lower alcohol containing 1–4 carbon atoms. A more preferred fixing reagent comprises a lower alcohol such as methanol, ethanol, propanol, or isopropanol optionally with a commonly employed organic acid. Such organic acids include without limitation acetic acid, citric acid, sulfosalicylic acid and trichloroacetic acid. In a most preferred embodiment, the fixing reagent consists of about 40% ethanol, about 10% acetic acid and about 50% distilled water by volume. Typically, a matrix may be fixed by immersion into a fixing reagent, and the immersion in fresh fixing reagent may be repeated up to 3 times.

Incubation time with the fixing reagent is determined empirically and depends on the thickness of the matrix and the temperature at which the incubation is conducted. Enhancement in the rate of fixing may be achieved by heating the matrix submerged in the fixing solution, e.g. using a microwave generator. For room temperature fixations using a 8 cm×8 cm×0.1 cm gel, the optimum fixing time is about 60 minutes on a platform rotator at 60 revolutions/min. One of ordinary skill in the art can determine the optimum time and temperature for fixing a given matrix with no more than routine experimentation.

The matrix may then be treated with a washing solution to remove as much of the free acid as possible. The washing solution may comprise water, about 10%–30% aqueous ethanol/methanol or about 10–30% aqueous ethanol/methanol, further comprising a buffer to neutralize residual acid in the matrix. A preferred wash is 30% ethanol in water. Typical incubation time for the matrix in the wash solution is about 10 min. If microwave heating is employed a shorter time of 2–5 min is preferred. In a preferred embodiment, the matrix is immersed in the washing solution for a time sufficient to remove agents that adversely affect staining.

The matrix is then contacted with a sensitizing reagent. The sensitizing reagent comprises at least one optionally substituted heteroaromatic compound, preferably having at least two heteroatoms and being water soluble and, optionally, one or more contrast enhancing agents and buffers.

Optionally substituted heteroaromatic compounds having at least two heteroatoms include those groups having 5 to 24 ring atoms; 6, 10 or 14 π electrons shared in a cyclic array; and containing carbon atoms and 2, 3 or 4 oxygen, nitrogen and/or sulfur atoms. Examples of such heteroaromatic compounds include without limitation thianthrene, phenoxathiin, imidazole, pyrazole, pyrazine, pyrimidine, pyridazine, indazole, purine, phthalzine, naphthyridine, quinoxaline, 1,4-dihydroquinoxaline-2,3-dione, quinozaline, cinnoline, pteridine, β-carboline, perimidine, phenanthroline, phenazine, isothiazole, phenothiazine, isoxazole, furazan, phenoxazine, pyrido[1,2-a]pyrimidin-4-one, 1,2-benzoisoxazole, benzimidazole, and benzothiazole. Optional substitutents include 1, 2, 3, or 4 alkyl, halo, haloalkyl, nitro, amino, cyano, isocyano, hydroxy, thiol, alkoxy, sulfonyl, carboxy, optionally substituted aryl and optionally substituted heteroaromatic groups. Preferred substituents include those which impart water solubility to the compound, e.g. amino, hydroxy, sulfonyl and carboxy groups. Heteroaromatic groups include those heteroaromatic groups listed above as well as thienyl, benzothienyl, naphthothienyl, furyl, pyranyl, chromanyl, isochromanyl, chromenyl, pyrrolyl, pyridyl, indolyl, quinolinyl, isoquinolinyl, coumarinyl, and carbazolyl groups and the like.

Useful alkyl groups are $C_{1-20}$ alkyl groups including methyl, ethyl, propyl, isopropyl, butyl, sec-butyl, t-butyl, pentyl, hexyl, octyl, decyl, dodecyl, octadecyl groups and the like. Lower alkyl groups are $C_{1-4}$ alkyl groups.

Useful halo groups include fluoro, chloro, bromo and iodo groups.

Useful haloalkyl groups include chloromethyl, bromomethyl, trifluoromethyl, trichloromethyl, pentachloromethyl, and pentafluoromethyl.

Useful amino groups include —$NH_2$ as well as mono- and dialkylamino groups such as methylamino, dimethylamino, ethylamino, propylamino, isopropylamino, butylamino and the like.

Useful aryl groups include are $C_{6-14}$ aryl, especially $C_{6-10}$ aryl. Typical $C_{6-14}$ aryl groups include phenyl, naththyl, phenanthryl, anthracyl, indenyl, biphenyl, biphenylenyl and fluorenyl groups.

Preferred optionally substituted heteroaromatic compounds are substituted benzothiazoles having the formula:

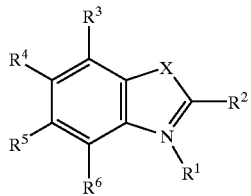

wherein X may be oxygen, $NR^7$ or sulfur, wherein $R^7$ is hydrogen or alkyl;

$R^1$ is missing or is a lower alkyl group;

$R^2$ is hydrogen, amino, optionally substituted lower alkyl, lower alkoxy, optionally substituted aryl, optionally substituted heteroaryl, optionally substituted aralkyl, optionally substituted heteroaralkyl, optionally substituted lower alkylthio, optionally substituted arylthio, optionally substituted heteroarylthio, 2-amino-α-(methoxyimino)-4-thiazolethiolacetate, guanidino, carboxy, alkylcarboxy, optionally substituted ureido, acetoacetamido, p-toluensulfonamidyl, or lower alkanoyloxy; and $R_3$–$R_6$ independently is hydrogen, amino, halo, nitro, cyano, isocyano, hydroxy, sulfonyl, carboxy, optionally substituted alkyl, alkoxy, optionally substituted aryl, optionally substituted heteroaryl, optionally substituted aralkyl, optionally substituted heteroaralkyl, optionally substituted lower alkylthio, optionally substituted arylthio, optionally substituted heteroarylthio, guanidino, optionally substituted ureido, or lower alkanoyloxy. Preferred $R_3$–$R_6$ groups include those which impart water solubility to the compounds. Also preferred are compounds wherein $R^1$ is missing.

Examples of optionally substituted heteroaromatic compounds that may be used in the practice of the invention include primuline, thioflavin S, 2-(4-aminophenyl)-6-methyl-7-sulfobenzothiazole, Direct Yellow 8, Direct Yellow 9, Direct Yellow 27, S-2-benxothiazolyl-2-amino-α-(methoxyimino)-4-thiazolethiolacetate, 3-(2-benzothiazolyl)-1-propanesulfonic acid (and its salts), 3-(2-benzothiazolyl)-7-(diethylamino)coumarin, 3-(2-benzimidazolyl)-7-(diethyl-amino)coumarin, 3-(2-benzothiazolyl)-7-octadecyloxycourmarin, 7-octadecyloxy-3-[3-(3-sulfopropyl)-2-benzothiazolylio]coumarin, 3-(2-benzothiazolyl)umbelliferone, (2-benzothiazolyl)guanidine, 2,6-dimethoxy-4-(2-benzothiazolyl)phenol, 2-(2-benzothiazolyl)ethanol, 2-(4-aminophenyl)-6-methylbenzothiazole, 2-benzothiazole sulfide, 2-benzothiazolylsulfonic acid (and its salts), 3-(2-benzothiazolylamino)-5-nitrophenol, 3-(2-benzothiazolyl)proprionitrile, 4-(6-methyl-2-benzothiazolyl)acetanilide, 4-(2-benzothiazolylthio)butyric acid (and its salts), 4-(6-methyl-2-benzothiazolyl)phenyl isocyanate, luciferin, ethyl (2-benzothiazolylthio)formate, N-(2-benzothiazolyl)acetoacetamide, N-(2-methyl-6-benzothiazolyl)acetamide, N-(3-(2-benzothiazolyl)-4-hydroxyphenyl)-p-toluenesulfonamide, and N-(6-nitro-2-benzothiazolyl)acetamide, many of which are available from Aldrich, Milwaukee, Wis.

Where the optionally substituted heteroaromatic compound is substituted by a carboxy or sulfonyl group, the group may be in the form of a salt, e.g. the sodium, potassium or ammonium salt. In the matrix, the cation of the salt may be replaced with a positively charge side chain from the protein. In addition, amino groups on a protein/polypeptide may form coordination complexes with metals such as silver. However, since these amino groups also react with anionic molecules added to the matrix, the ability of proteins/polypeptides to coordinate to silver ions will be drastically altered. However, if the heteroaromatic compound contains an additional group capable of binding silver, the chelating property of the complex will be retained. The formation of salt complexes between positive protein side chains of proteins/peptides and the negative sulfonate substituted sensitizers leads to sensitivity advantages over other silver staining methods, particularly for low molecular weight proteins.

Many of the polyaminobenzothiazole sulfonic acid derivatives are dark colored materials. These materials are not suitable for silver staining because of the residual dark color left in the matrix giving the appearance of a heightened background. Thus, in a preferred embodiment, the optionally substituted heteroaromatic compound is not black or very dark in color when in solution. Primuline and thioflavin S are typically brown colored solids. However in concentrated solutions, they are orange and, when diluted, are a yellow color.

Examples of contrast enhancing agents include sodium sulfide, thiourea, dithiothreitol, potassium tetrathionate, sodium dithionite, and the sodium or potassium salt of thiosulfate. Sodium thiosulfate is known to act as a contrast enhancing agent. (Wood, H. W., *J. Phot. Sci.* 2: 154 (1954)). The silver deposited in the biopolymer within a matrix is more easily reduced in the presence of sulfur containing compounds. It is believed that silver sulfide acts as a catalyst for the reduction of silver ions. In a preferred embodiment, the contrast enhancing agent is present at a concentration of about 0.05% to 0.25%.

Examples of buffers that may be used in the practice of the invention include known biological buffers with pKa's from about 5–10. See the Sigma Life Sciences Catalog, 2000–2001, pp. 962–965. Preferred buffers are aqueous morpholinoethanesulfonic acid, morpholinopropanesulfonic acid (MOPS), 4-(2-hydroxyethyl)-1-piperazinepropanesulfonic acid (EPPS), 4-(2-hydroxyethyl)-1-piperazineethanesulfonic acid (HEPES), and the like.

A preferred sensitizing reagent comprises about 0.1 M morpholinoethanesulfonic acid (MES), about 5 mM sodium thiosulfate, and about 0.025% primuline. The sensitizing reagent may further comprise about 30% ethanol in water. Another preferred sensitizing reagent comprises about 0.1 M MES, about 5 mM sodium thiosulfate pentahydrate, about 0.025 g/L thioflavin S, and about 1% dimethylformamide (DMF). In order to prepare this reagent, thioflavin S is dissolved in DMF and an insoluble impurity is removed. This solution is then added to a solution of MES and thiosulfate, titrated to pH 6.1. Although a salt precipitates, it does not affect the performance of the reagent. Alternatively, thioflavin S, MES and thiosulfate may be dissolved in water to give a solution without any DMF. This reagent is not preferred as it does not work as well when the reaction is heated with microwave energy. Putting DMF back into the solution restores the performance, but brings back the precipitate.

Next, the matrix is contacted with a stainer solution comprising one or more photosensitive or reduceable metal salts, optionally with actuating irradiation, to stain the biopolymer or form a stain image. Preferably, the reduceable metal salt has a reduction potential of about 0.5 to about 1.9 volts. Examples of such reduceable metal salts include silver, gold, platinum and/or iridium salts. Silver salts are preferred because they are less costly. Silver nitrate is a most preferred reduceable metal salt. Alternatively, a silver ammonia complex, e.g. prepared with silver nitrate and ammonium hydroxide, may be employed. The concentration of the salt in water is inversely (but not proportionally) dependent on the thickness of the matrix. Thus, an ultrathin matrix of 0.001 mm or less requires higher concentrations of the reduceable metal salt(s), while thicker matrixes require lower concentrations. See U.S. Pat. No. 4,405,720. A typical concentration is 0.1–0.2% silver nitrate in distilled water. The matrix is incubated from about 10–60 minutes with about 15 minutes being a preferred time. When microwave heating is employed, the incubation time may be reduced to five minutes including the time of irradiation.

The use of light irradiation can be used when the matrix thickness is greater than about 1 mm or when staining certain organic polymers such as DNA. The irradiation may be in any conventional manner and must be sufficient to effect the photochemical reaction. Light radiation from actinic through infrared and/or heat may be employed. When used, the irradiation is preferably during the first minutes of treatment with the reduceable salt(s), to produce maximum sensitivity. Typically, a bright uniform light source such as a 160 watt fluorescent grid lamp which emits light equivalent to a 1,500 watt tungsten source may be used. One of ordinary skill in the art can select an optimum light source and time of irradiation for a given matrix, protein/polypeptide and nucleic acid molecule with no more than routine experimentation.

Next the matrix is quickly rinsed with water to remove the free reduceable metal salt(s). Since silver binding is reversible the time of rinsing should be kept to about 1 minute or less.

Next, the stain image is developed. This may be accomplished by contacting the matrix with a developer solution comprising one or more reducing agents. Such reducing agents include any that are used in photography including metallic compounds of iron, tungsten, vanadium and molybdenum, and organic compounds including hydroquinone, pyrogallol, p-phenylenediamine, paraformaldehyde and formaldehyde. Organic reducing reagents are preferred. When formaldehyde or paraformaldehyde is the reducing agent, it is preferred to further add an alkalinizing agent such as sodium carbonate or sodium metaborate to the solution. Since the latent image development may continue until the matrix is contacted with the reducing agent(s), one may immerse the matrix immediately into the reducing agent as soon as it is removed from the reduceable metal salt containing solution.

In a preferred embodiment, the matrix is immersed in a basic buffer solution whose pH is between 11 and 12 and which contains formaldehyde. Preferred buffers include sodium and potassium carbonate. The immersion may be repeated as necessary or desired. Optionally, the matrix may be subjected to gentle agitation. A most preferred developer solution consists of 2.5% potassium carbonate and 0.35% formaldehyde (37% by weight) in distilled water. The development time is from about 3–30 minutes depending upon the thickness of the gel, the extent of sample loading and background staining intensity. One of ordinary skill in the art can determine the optimum development time with no more than routine experimentation.

Finally, the reaction in the matrix is stopped with a stopper solution. This may be accomplished by thorough washing with water and/or by lowering the pH of the developer to between 7–10 and complexation of the unreduced silver with a chelating agent. For convenience a stopper solution comprising a buffer or an acid and chelating agent may be added directly to the developer solution. Examples of acids that may be used include aqueous solutions of acetic, citric and hydrochloric acid. Examples of chelating agents include ethylenediamine tetraacetic acid. A preferred chelation agent that also functions as a buffer is ethylenediamine tetraacetic acid and its salts. A preferred stopper solution is 0.5 M ethylenediamine tetraacetic acid trisodium salt, pH 8. Typically the matrix is submerged in the stopper solution for ten minutes, optionally with gentle agitation, and then washed with distilled water. One of ordinary skill in the art can determine optimum time and conditions for stopping development of the latent image with no more than routine experimentation.

Once the stain image has been developed, it can be detected by any conventional means for detection including visual inspection, scanning, e.g. with a conventional flatbed scanner, or with an imaging camera. See, for example, U.S. Pat. No. 4,703,016.

The invention also relates to a method for identifying a protein or peptide in a matrix, comprising:

(a) contacting the matrix with a sensitizing reagent comprising one or more optionally substituted heteroaromatic compounds;

(b) contacting the matrix with one or more reduceable metal salts to stain said protein or peptide;

(c) detecting the stained protein or peptide and thereby the protein or peptide;

(d) carrying out a cleavage reaction on the protein or peptide to give fragments; and (e) carrying out a mass spectrometric analysis on said fragments thereby identifying the protein or peptide.

In carrying out this method, the protein or peptide may be first fixed to the matrix as described herein. In a preferred embodiment, the protein or peptide is fixed to the matrix by contacting the matrix with a fixing reagent consisting of ethanol, acetic acid and water.

Before the stain protein or peptide is detected, it may be treated with a developing solution as described herein which comprises one or more reducing agents. The stain image may then be detected according to any of the methods described herein.

In order to carry out a cleavage reaction on the protein or peptide, the stain protein or peptide may be excised from the matrix and the protein or peptide isolated from the matrix. For example, the protein or peptide may be excised from the matrix with a scalpel and placed into a container. In a preferred embodiment, an aqueous mixture of potassium ferricyanide and sodium thiosulfate is added to the container to reoxidize substantially all of the reduced silver metal grains to silver ions and complex them to thiosulfate. The protein or polypeptide may be extracted with water from one up to six or more times. The extracts may then be treated with a cleavage reagent comprising a protease such as trypsin, and the fragments subjected to mass spectrometric analysis to determine identity. See Shevenko, A. et al., *Anal. Chem.* 68:850–858 (1996); Helmannn, V. et al., *Anal. Biochem.* 224:451–455 (1995); Coligan, J. E. et al., in Current Protocols in Protein Science, V. B. Chanda (ed.) (1998); Patterson, S. D. and Aebersold, R., *Electrophoresis* 16:1791–1814 (1995); and Bergman et al., *Electrophoresis* 21:679–686 (2000). As discussed above, this method is an improvement over prior methods using glutaraldehyde as no cross linking of the proteins and polypeptides occur. In addition, the sensitizing reagent provides for the sensitive detection of the proteins and polypeptides without the need for glutaraldehyde.

The present invention is a great advance in the art in that a new class of sensitizing agents has been discovered. These new agents bind to the biopolymers that have been fixed within a matrix and increase the localized binding of the reduceable metal salt to the biopolymer zone. These sensitizing agents only bind the reduceable metal salt ion weakly so that reduction of the ions may occur when the matrix is subjected to reducing conditions as described herein.

The increase in sensitivity for biopolymers achieved according to the present invention is believed to result from several factors discussed below. First, while not wishing to be bound by any particular theory, it is believed that the charge—charge attraction of the sulfonic acid groups of the thioflavin S with positively charged side chains and possibly interactions of the aromatic benzothiazole ring with hydrophobic regions of the protein structure allow binding of the sensitizer to the proteins within the matrix. In addition, it is believed that the sulfur and nitrogen atoms of the benzothiazole ring structure are capable of forming weak coordination complexes with silver(+1) ions which can then be reduced efficiently to silver metal with a dilute formaldehyde solution at a pH >10. For nucleic acids, it is believed that the mechanism is more likely an intercalation effect in which the planar aromatic nucleus of the benzothiazole ring structure aligns between two adjacent pyrimidine or purine bases to form a complex which is stabilized by pi stacking interactions. Again the silver binding occurs through the sulfur and/or nitrogen of the benzothiazole ring system and is bound weakly enough to be reduced by formaldehyde in alkali medium above pH 10.

The invention also relates to a kit for the detection of biopolymers, comprising one or more components selected from the group consisting of (a) a sensitizing reagent comprising one or more optionally substituted heteroaromatic compounds;

(b) one or more reduceable metal salts;

(c) one or more developer solutions comprising a reducing agent;

(d) one or more stopper solutions which prevent further reduction of the reduceable metal salts;

(e) one or more buffers;

(f) one or more fixing reagents;

(g) one or more cleaving reagents;

(h) one or more biopolymers;

(i) one or more matrixes; and (j) one or more indicators which are sensitive to pH changes.

The kit in general is a carton, box, tube or the like and contains one or more containers, each of which containing one or more of the components listed above. Such containers include boxes, bottles, jars, tubes, ampoules and the like.

Biopolymers may be included in the kit for use, for example, as standards or controls.

Examples of matrixes that may be included in the kit include polyacrylamide gel, agarose, paper, cellulose acetate, or nitrocellulose.

Examples of indicators that may be included in the kit include phenolphthalein and thymolphthalein.

The invention also relates to compositions for carrying out the methods of the present invention and to compositions made when carrying out the invention. Such compositions may comprise one or more components selected from the group consisting of (a) a sensitizing reagent comprising one or more optionally substituted heteroaromatic compounds;

(b) one or more reduceable metal salts;

(c) one or more developer solutions comprising a reducing agent;

(d) one or more stopper solutions which prevent further reduction of the reduceable metal salts;

(e) one or more buffers;

(f) one or more fixing reagents;

(g) one or more cleaving reagents;

(h) one or more biopolymers;

(i) one or more matrixes; and (j) one or more indicators which are sensitive to pH changes.

The invention also relates to the compositions obtained by the practice of the invention. Such compositions include, without limitation, the various reaction mixtures that are obtained as well as the cleaved proteins and peptides obtained with a cleaving reagent.

The following examples are illustrative, but not limiting, of the method and compositions of the present invention. Other suitable modifications and adaptations of the variety of conditions and parameters normally encountered in the art and which are obvious to those skilled in the art are within the spirit and scope of the invention.

EXAMPLES

Example 1

Basic Staining Procedure

In the following example, the formulations were made up as follows. All solutions were made w/ultrapure water.

| | | |
|---|---|---|
| Sensitizer: | 1 | M Morpholinoethane sulfonic acid |
| | 50 | mM Sodium thiosulfate pentahydrate |
| | 0.25 | g/L Thioflavin S |
| | 10% | Dimethylformamide |
| Stainer: | 20% | Silver nitrate |
| Developer: | 15% | Potassium carbonate |
| | 0.075% | Sodium thiosulfate pentahydrate |
| | 0.002% | Phenolphthalein |
| Developer Enhancer: | 37% | Formaldehyde |
| Stopper Solution: | 0.5 | M Ethylenediamine tetraacetic acid |
| | 1.5 | M Tris(hydroxymethyl)aminomethane |
| Destainer A: | 30 | mM Potassium Ferricyanide |
| Destainer B: | 100 | mM Sodium thiosulfate pentahydrate |

Basic Staining Protocol

Before starting, prepare the following solutions for staining:

| Sensitizing solution | |
|---|---|
| Ethanol | 30 ml |
| Sensitizer | 10 ml |
| Ultra pure water | to 100 ml |
| Staining solution | |
| Stainer | 1 ml |
| Ultra pure water | to 100 ml |
| Developing solution | |
| Developer | 10 ml |
| Developer enhancer | 1 drop |
| Ultra pure water | to 100 ml |

The solutions may be prepared immediately before starting the staining protocol or as one proceeds to the next step.

Procedure

This procedure is for use with an 8×8 cm NuPAGE® Bis-Tris, Tris-Acetate, TBE or Tris-Glycine mini-gel, 1.0 mm thick. If one stains two mini-gels, 1.0 mm thick or one large (18×18 cm) gel, all solution volumes should be doubled while maintaining the same incubation time. One may have to optimize the staining protocol, if the dimensions of the gel are not the same as mentioned above.

All incubations should be performed on a rotary shaker rotating at a speed of approximately 1 revolution/sec at room temperature. There should be 100 ml of solution per gel.

1. After electrophoresis, remove the gel from the cassette and place it in a clean staining tray of the appropriate size. Optionally, the gel may be rinsed twice with ultra pure water.
2. Fix the gel in 100 ml of fixative for 60 minutes with gentle rotation. (Note: The gel can be stored in the fixative overnight if there is not enough time to complete the staining protocol.)
3. Decant the fixative solution and wash the gel in 100 ml of 30% ethanol for 10 minutes.
4. Add 100 ml of Sensitizing solution to the washed gel in the staining container. Incubate the gel in the Sensitizing solution for 10 minutes.
5. Wash the gel in 100 ml of 30% ethanol for 10 minutes.
6. Decant the Sensitizing solution and wash the gel in 100 ml of ultra pure water for 10 minutes.
7. Place the gel in 100 ml of Staining solution for 15 minutes.
8. After staining is complete, decant the Staining solution and wash the gel with 100 ml of ultra pure water for 1 minute. Note: Washing the gel for more than a minute will remove silver ions from the gel and result in decreased sensitivity.
9. Incubate the gel in 100 ml of Developing solution for 5–8 minutes until bands start to appear.
10. Once the desired band intensity is achieved, immediately add 10 ml of Stopper directly to the gel still immersed in Developing solution. Gently agitate the gel for 10 minutes. The color changes from pink to colorless indicating that the development has stopped.
11. Decant the Stopper solution and wash the gel with 100 ml of ultra pure water for 10 minutes.

If one is to destain the gel for mass spectrometry analysis, see Example3.

Example 2

Fast Staining Procedure

Introduction

The fast staining protocol is a modification of the basic staining protocol. This method uses a microwave oven to rapidly silver stain protein gels. This staining protocol can be completed in less than an hour.

| Materials Needed |
|---|
| Ultra pure water |
| Microwaveable staining tray |
| Microwave |
| Rotary shaker |
| Teflon coated stir bars |
| Disposable 10 ml pipettes |
| Clean glass bottles for reagent preparation |
| Graduated Glass Cylinders |
| 30% ethanol (made with ultra pure water) |
| 100% ethanol |
| Fixative (40% ethanol, 10% acetic acid, made with ultra pure water) |

Before Starting

Prepare the following solutions for staining:

| Sensitizing solution | |
|---|---|
| Ethanol | 30 ml |
| Sensitizer | 10 ml |
| Ultra pure water | to 100 ml |

-continued

| Staining solution | |
| --- | --- |
| Stainer | 1 ml |
| Ultra pure water | to 100 ml |
| Developing solution | |
| Developer | 10 ml |
| Developer enhancer | 1 drop |
| Ultra pure water | to 100 ml |

Note:
One may prepare all solutions immediately before starting the staining protocol or prepare them as one proceeds to the next step.

Procedure

For use with an 8×8 cm NuPAGE® gel, 1.0 mm thick. Be sure to have 100 ml of solution per gel. (Note: One may have to optimize the staining protocol, if the dimensions of your the are not the same as mentioned above.)

1. After electrophoresis, remove the gel from the cassette and place it in a clean microwaveable staining tray of appropriate size. Rinse the gel twice with ultra pure water.
2. Place the gel in 100 ml of fixative and microwave at high power for 30 seconds. Remove the gel from the microwave and gently agitate it for 5 minutes at room temperature. Decant the fixative.
3. Wash the gel with 100 ml of 30% ethanol in a microwave at high power for 30 seconds. Remove the gel from the microwave and gently agitate it for 5 minutes at room temperature on a rotary shaker.
4. Add 100 ml of Sensitizing solution to the washed gel. Microwave the gel at high power for 30 seconds. Remove the gel from the microwave and place it on a rotary shaker for 2 minutes at room temperature. Decant the sensitizing solution.
5. Wash the gel twice in 100 ml ultra pure water. Microwave at high power for 30 seconds. Remove the gel from the microwave and gently agitate it for 2 minutes at room temperature. Decant the water.
6. Place the gel in 100 ml of Staining solution. Microwave at high power for 30 seconds. Remove the gel from the microwave and gently agitate it for 5 minutes at room temperature.
7. Decant the Staining solution and wash the gel with 100 ml of ultra pure water for 1 minute.
8. Place the gel in 100 ml of Developing solution and incubate for 5 minutes with gentle agitation on a rotary shaker. (Do not microwave).
9. Once the desired band intensity is achieved, immediately add 10 ml of Stopper directly to the gel still immersed in Developing solution and gently agitate the gel for 10 minutes. The color changes from pink to clear indicating that the development has stopped.
10. Wash the gel with 100 ml of ultra pure water for 10 minutes.
11. If one must destain the gel for mass spectrometry analysis, see Example 3.

Example 3

Destaining Procedure for Mass Spectrometric Analysis

When preparing samples for mass spectrometry analysis, it is important to remove silver ions from protein bands before performing in-gel trypsin digestion (Gharahdaghi et al., *Electrophoresis* 20:601–605 (1999)). A destaining protocol to effectively remove silver ions from the gel is described below.

Materials Needed:
Clean scalpel
1.5 ml sterile microcentrifuge tubes
Ultra pure water
Microcentrifuge Procedure For use with NuPAGE® Bis Tris, Tris-Glycine or Tris-Acetate 8×8 mini-gels, 1.0 mm thick.

1. After silver staining of the gel, wash the gel thoroughly with ultra pure water.
2. Carefully excise the band(s) of interest using a clean scalpel and place into 1.5 ml sterile microcentrifuge tube(s). Excise another piece of gel of the same size from a blank region of the gel and place into another sterile microcentrifuge tube. This will be used later as a control for trypsin digestion.
3. Add 50 $\mu$l of Destainer A and 50 $\mu$l of Destainer B to each microcentrifuge tube.

Note: If destaining a large number of gel bands, then prepare the required amount of the destaining solution by mixing Destainer A and B, and use immediately. Destainer solutions A and B cannot be stored for long periods once they are mixed.

1. Mix the contents of the tube thoroughly and incubate for 15 minutes at room temperature.
2. Carefully remove the supernatant using a clean pipette tip.
3. Add 200 $\mu$l of ultra pure water to the tube and mix thoroughly. Incubate for 10 minutes at room temperature.

Repeat steps 5–6 at least two times. Proceed to trypsin digestion and analysis by mass spectrometry.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A method for detecting a biopolymer in a matrix, comprising:
    (a) contacting the matrix with a sensitizing reagent comprising one or more optionally substituted heteroaromatic compounds;
    (b) contacting the matrix with one or more reduceable metal salts to stain said biopolymer; and
    (c) detecting the stained biopolymer.

2. The method of claim 1, wherein said matrix is a polyacrylamide gel, agarose, paper, cellulose acetate, or nitrocellulose.

3. The method of claim 1, wherein said biopolymer is fixed to the matrix before (a) by treatment of the matrix with a fixing reagent comprising an aqueous solution of an organic acid and a lower alcohol containing 1–4 carbon atoms.

4. The method of claim 3, wherein said lower alcohol is methanol, ethanol, propanol, or isopropanol.

5. The method of claim 3, wherein said organic acid is acetic acid, citric acid, sulfosalicylic acid or trichloroacetic acid.

6. The method of claim 3, wherein said fixing reagent consists of about 40% ethanol, about 10% acetic acid and about 50% distilled water by volume.

7. The method of claim 1, wherein said substituted heteroaromatic compound is substituted with a group which imparts water solubility.

8. The method of claim 1, wherein said optionally substituted heteroaromatic compound is primuline, thioflavin S or 2-(4-aminophenyl)-6-methyl-7-sulfobenzothiazole.

9. The method of claim 1, further comprising contacting said matrix with said sensitizing reagent together with one or more contrast enhancing agents and one or more buffers.

10. The method of claim 9, wherein said contrast enhancing agents are selected from the group consisting of sodium sulfide, thiourea, dithiothreitol, potassium tetrathionate, sodium dithionite, and the sodium or potassium salt of thiosulfate.

11. The method of claim 9, wherein said one or more buffers has a pKa of 5–10.

12. The method of claim 9, wherein said one or more buffers is aqueous morpholinoethanesulfonic acid.

13. The method of claim 1, wherein said one or more reduceable metal salts is silver nitrate.

14. The method of claim 1, wherein said stained biopolymer is developed prior to said detecting by contacting the matrix with one or more reducing agents.

15. The method of claim 14, wherein said one or more reducing agents is formaldehyde.

16. The method of claim 1, wherein said stained biopolymer is detected visually.

17. The method of claim 1, wherein said stained biopolymer is detected with an electronic scanner.

18. The method of claim 1, wherein said stained biopolymer is detected with an imaging camera.

19. The method of claim 1, wherein said matrix is heated when contacted with at least one of the sensitizing reagent and the one or more reduceable metal salts.

20. The method of claim 19, wherein said heating is carried out with microwave energy.

21. The method of claim 1, wherein said biopolymer is a protein.

22. The method of claim 1, wherein said biopolymer is a peptide.

23. The method of claim 1, wherein said biopolymer is a nucleic acid molecule.

24. A method for detecting a protein/peptide or nucleic acid molecule in a polyacrylamide gel, comprising:
(a) fixing the protein/peptide or nucleic acid molecule to the polyacrylamide gel;
(b) contacting the polyacrylamide gel with a sensitizing reagent comprising primuline, thioflavin S or 2-(4-aminophenyl)-6-methyl-7-sulfobenzothiazole;
(c) contacting the polyacrylamide gel with an aqueous solution of a silver salt to stain the protein/peptide or nucleic acid molecule,
(d) developing the stained protein/peptide or nucleic acid molecule, and
(e) detecting the stained protein/peptide or nucleic acid molecule.

25. The method of claim 24, wherein said protein/peptide or nucleic acid molecule is fixed to the polyacrylamide gel by contacting the polyacrylamide gel with a fixing reagent consisting of about 40% ethanol, about 10% acetic acid and about 50% distilled water by volume.

26. The method of claim 24, wherein said sensitizing reagent further comprises aqueous morpholinoethanesulfonic acid and one or more contrast enhancing agents selected from the group consisting of sodium sulfide, thiourea, dithiothreitol, potassium tetrathionate, sodium dithionite, and the sodium or potassium salt of thiosulfate.

27. The method of claim 24, wherein said stained protein/peptide or nucleic acid molecule is developed by contacting the polyacrylamide gel with aqueous formaldehyde.

28. A method for identifying a protein or peptide in a matrix, comprising:
(a) contacting the matrix with a sensitizing reagent comprising one or more optionally substituted heteroaromatic compounds;
(b) contacting the matrix with one or more reduceable metal salts to stain said protein or peptide;
(c) detecting the stained protein or peptide;
(d) carrying out a cleavage reaction on the protein or peptide to give fragments; and
(e) carrying out a mass spectrometric analysis on said fragments thereby identifying the protein or peptide.

29. A composition, comprising:
(a) a sensitizing reagent comprising one or more optionally substituted heteroaromatic compounds;
(b) one or more reduceable metal salts;
(c) one or more developer solutions comprising a reducing agent;
(d) one or more stopper solutions which prevent further reduction of the reduceable metal salts;
(e) one or more contrast enhancing agents;
(f) one or more buffers;
(g) one or more fixing reagents;
(i) one or more biopolymers;
(j) one or more matrixes; and
(k) phenolphthalein or thymolphthalein.

30. A composition, comprising:
(a) a sensitizing reagent comprising one or more optionally substituted heteroaromatic compounds;
(b) one or more reduceable metal salts;
(c) one or more developer solutions comprising a reducing agent;
(d) one or more stopper solutions which prevent further reduction of the reduceable metal salts;
(e) one or more contrast enhancing agents;
(f) one or more buffers;
(g) a fixing reagent comprising an aqueous solution of an organic acid and a lower alcohol containing 1–4 carbon atoms;
(i) one or more biopolymers;
(j) one or more matrixes; and
(k) one or more indicators which are sensitive to pH changes.

31. The composition of claim 30, wherein said lower alcohol is methanol, ethanol, propanol, or isopropanol.

32. The composition of claim 30, wherein said organic acid is acetic acid, citric acid, sulfosalicylic acid or trichloroacetic acid.

33. A composition, comprising:
(a) a sensitizing reagent comprising one or more optionally substituted heteroaromatic compounds;
(b) one or more reduceable metal salts;
(c) one or more developer solutions comprising a reducing agent;
(d) one or more stopper solutions which prevent further reduction of the reduceable metal salts;

(e) one or more contrast enhancing agents;

(f) one or more buffers;

(g) a fixing reagent consisting of about 40% ethanol, about 10% acetic acid and about 50% distilled water by volume;

(i) one or more biopolymers;

(j) one or more matrixes; and (k) one or more indicators which are sensitive to pH changes.

34. A composition, comprising:

(a) a sensitizing reagent comprising one or more optionally substituted heteroaromatic compounds, wherein said optionally substituted heteroaromatic compounds are primuline, thioflavin S or 2-(4-aminophenyl)-6-methyl-7-sulfobenzothiazole;

(b) one or more reduceable metal salts; and (c) one of more developer solutions comprising a reducing agent.

35. A composition, comprising:

(a) a sensitizing reagent comprising one or more optionally substituted heteroaromatic compounds wherein said optionally substituted heteroaromatic compounds are primuline, thioflavin S or 2-(4-aminophenyl)-6-methyl-7-sulfobenzothiazole;

(b) one or more developer solutions comprising a reducing agent; and (c) one or more contrast enhancing agents selected from the group consisting of sodium sulfide, thiourea, dithiothreitol, potassium tetrathionate, sodium dithionite, and the sodium or potassium salt of thiosulfate.

36. A composition, comprising:

(a) a sensitizing reagent comprising one or more optionally substituted heteroaromatic compounds;

(b) one or more reduceable metal salts;

(c) one or more stopper solutions which prevent further reduction of the reduceable metal salts; and (d) one or more contrast enhancing agents selected from the group consisting of sodium sulfide, thiourea, dithiothreitol, potassium tetrathionate, sodium dithionite, and the sodium or potassium salt of thiosulfate.

37. A composition, comprising:

(a) a sensitizing reagent comprising one or more optionally substituted heteroaromatic compounds;

(b) one or more reduceable metal salts;

(c) one or more developer solutions comprising a reducing agent;

(d) one or more stopper solutions which prevent further reduction of the reduceable metal salts;

(e) one or more contrast enhancing agents selected from the group consisting of sodium sulfide, thiourea, dithiothreitol, potassium tetrathionate, sodium dithionite, and the sodium or potassium salt of thiosulfate;

(f) one or more buffers;

(g) one or more fixing reagents;

(i) one or more biopolymers;

(j) one or more matrixes; and (k) one or more indicators which are sensitive to pH changes.

38. A composition, comprising:

(a) a sensitizing reagent comprising one or more optionally substituted heteroaromatic compounds;

(b) one or more reduceable metal salts;

(c) one or more developer solutions comprising a reducing agent;

(d) one or more stopper solutions which prevent further reduction of the reduceable metal salts;

(e) one or more contrast enhancing agents;

(f) one or more buffers having a pKa of 5–10;

(g) one or more fixing reagents;

(i) one or more biopolymers;

(j) one or more matrixes; and (k) one or more indicators which are sensitive to pH changes.

39. A composition, comprising:

(a) a sensitizing reagent comprising one or more optionally substituted heteroaromatic compounds;

(b) one or more reduceable metal salts;

(c) one or more developer solutions comprising a reducing agent;

(d) one or more stopper solutions which prevent further reduction of the reduceable metal salts;

(e) one or more contrast enhancing agents;

(f) one or more buffers selected from the group consisting of morpholinoethanesulfonic acid, 4-(2-hydroxyethyl)-1-piperazinepropane-sulfonic acid (EPPS) and 4-(2-hydroxy-ethyl)-1-piperazineethanesulfonic acid (HEPES);

(g) one or more fixing reagents;

(i) one or more biopolymers;

(j) one or more matrixes; and (k) one or more indicators which are sensitive to pH changes.

40. A composition, comprising:

(a) a sensitizing reagent comprising one or more optionally substituted heteroaromatic compounds;

(b) one or more reduceable metal salts;

(c) one or more stopper solutions which prevent further reduction of the reduceable metal salts; and (d) one or more contrast enhancing agents.

41. The composition of claim 40 further comprising:

(e) one or more developer solutions comprising a reducing agent;

(f) one or more buffers;

(g) one or more fixing reagents;

(i) one or more biopolymers;

(j) one or more matrixes; and (k) one or more indicators which are sensitive to pH changes.

42. The composition of claim 40, wherein said one or more reduceable metal salts is silver nitrate.

43. A kit for the detection of biopolymers, comprising:

(a) a sensitizing reagent comprising one or more optionally substituted heteroaromatic compounds;

(b) one or more reduceable metal salts;

(c) one or more developer solutions comprising a reducing agent;

(d) one or more stopper solutions which prevent further reduction of the reduceable metal salts;

(e) one or more contrast enhancing agents;

(f) one or more buffers;

(g) one or more fixing reagents;
(h) one or more cleaving reagents;
(i) one or more biopolymers;
(j) one or more matrixes; and
(k) phenolphthalein or thymolphthalein.

44. A kit for the detection of biopolymers, comprising:
(a) a sensitizing reagent comprising one or more optionally substituted heteroaromatic compounds;
(b) one or more reduceable metal salts;
(c) one or more developer solutions comprising a reducing agent;
(d) one or more stopper solutions which prevent further reduction of the reduceable metal salts;
(e) one or more contrast enhancing agents;
(f) one or more buffers;
(g) a fixing reagent comprising an aqueous solution of an organic acid and a lower alcohol containing 1–4 carbon atoms;
(h) one or more cleaving reagents;
(i) one or more biopolymers;
(j) one or more matrixes; and
(k) one or more indicators which are sensitive to pH changes.

45. The kit of claim 44, wherein said lower alcohol is methanol, ethanol, propanol, or isopropanol.

46. The kit of claim 44, wherein said organic acid is acetic acid, citric acid, sulfosalicylic acid or trichloroacetic acid.

47. A kit for the detection of biopolymers, comprising:
(a) a sensitizing reagent comprising one or more optionally substituted heteroaromatic compounds;
(b) one or more reduceable metal salts;
(c) one or more developer solutions comprising a reducing agent;
(d) one or more stopper solutions which prevent further reduction of the reduceable metal salts;
(e) one or more contrast enhancing agents;
(f) one or more buffers;
(g) a fixing reagent consisting of about 40% ethanol, about 10% acetic acid and about 50% distilled water by volume;
(h) one or more cleaving reagents;
(i) one or more biopolymers;
(j) one or more matrixes; and
(k) one or more indicators which are sensitive to pH changes.

48. A kit for the detection of biopolymers, comprising:
(a) a sensitizing reagent comprising one or more optionally substituted heteroaromatic compounds;
(b) one or more reduceable metal salts;
(c) one or more developer solutions comprising a reducing agent;
(d) one or more stopper solutions which prevent further reduction of the reduceable metal salts;
(e) one or more contrast enhancing agents selected from the group consisting of sodium sulfide, thiourea, dithiothreitol, potassium tetrathionate, sodium dithionite, and the sodium or potassium salt of thiosulfate;
(f) one or more buffers;
(g) one or more fixing reagents;
(h) one or more cleaving reagents;
(i) one or more biopolymers;
(j) one or more matrixes; and
(k) one or more indicators which are sensitive to pH changes.

49. A kit for the detection of biopolymers, comprising:
(a) a sensitizing reagent comprising one or more optionally substituted heteroaromatic compounds;
(b) one or more reduceable metal salts;
(c) one or more developer solutions comprising a reducing agent;
(d) one or more stopper solutions which prevent further reduction of the reduceable metal salts;
(e) one or more contrast enhancing agents;
(f) one or more buffers having a pKa of 5–10;
(g) one or more fixing reagents;
(h) one or more cleaving reagents;
(i) one or more biopolymers;
(j) one or more matrixes; and
(k) one or more indicators which are sensitive to pH changes.

50. A kit for the detection of biopolymers, comprising:
(a) a sensitizing reagent comprising one or more optionally substituted heteroaromatic compounds;
(b) one or more reduceable metal salts;
(c) one or more developer solutions comprising a reducing agent;
(d) one or more stopper solutions which prevent further reduction of the reduceable metal salts;
(e) one or more contrast enhancing agents;
(f) one or more buffers selected from the group consisting of morpholinoethanesulfonic acid, 4-(2-hydroxyethyl)-1-piperazinepropane-sulfonic acid (EPPS) and 4-(2-hydroxy-ethyl)-1-piperazineethanesulfonic acid (HEPES);
(g) one or more fixing reagents;
(h) one or more cleaving reagents;
(i) one or more biopolymers;
(j) one or more matrixes; and
(k) one or more indicators which are sensitive to pH changes.

51. A kit for the detection of biopolymers, comprising:
(a) a sensitizing reagent comprising one or more optionally substituted heteroaromatic compounds wherein said optionally substituted heteroaromatic compounds are primuline, thioflavin S or 2-(4-aminophenyl)-6-methyl-7-sulfobenzothiazole; and
(b) silver nitrate.

* * * * *